United States Patent [19]

Mazars et al.

[11] Patent Number: 4,815,457
[45] Date of Patent: Mar. 28, 1989

[54] ADHESIVE DRESSING FOR EASY APPLICATION TO SKIN

[75] Inventors: Paul Mazars, Louviers; Jean-Pierre Barreteau, St Aubin D'Ecrosville, both of France

[73] Assignee: Beghin-Say S.A., Thumeries, France

[21] Appl. No.: 852,640

[22] PCT Filed: Jun. 13, 1985

[86] PCT No.: PCT/FR85/00148

§ 371 Date: Feb. 24, 1986

§ 102(e) Date: Feb. 24, 1986

[87] PCT Pub. No.: WO86/00220

PCT Pub. Date: Jan. 16, 1986

[30] Foreign Application Priority Data

Jun. 25, 1984 [FR] France ................................ 84 09963

[51] Int. Cl.⁴ ........................ A61F 13/00; A61F 15/00
[52] U.S. Cl. ..................................... 128/155; 128/156; 604/304; 604/307; 206/440; 206/441
[58] Field of Search ........................ 128/156, 154, 155; 604/304, 307; 206/440, 441

[56] References Cited

U.S. PATENT DOCUMENTS

| | | | |
|---|---|---|---|
| 2,473,062 | 6/1949 | Kennedy et al. | 128/156 |
| 3,018,881 | 1/1962 | Wall | 206/441 |
| 3,119,495 | 1/1964 | Pratt | 206/440 |
| 3,899,077 | 8/1975 | Spiegelberg | 206/820 |
| 4,094,316 | 6/1978 | Nathanson | 128/156 |
| 4,304,333 | 12/1981 | Kozlow, Sr. | 206/441 |
| 4,545,372 | 10/1985 | Lauritzen | 128/156 |
| 4,552,802 | 11/1985 | Machin | 128/156 |

*Primary Examiner*—Richard J. Apley
*Assistant Examiner*—Paul Prebilic
*Attorney, Agent, or Firm*—A. W. Breiner

[57] ABSTRACT

The present invention relates to an adhesive dressing 1, coated on one surface with a pressure-sensitive adhesive 3 and covered with a non-adhesive support 4. The dressing 1 is folded back on itself on the side of the protective support 4 along a transverse fold 5, to give two parts 1a and 1b. The protective support 4a of one of the two parts 1a is cut along a line 6 parallel to the fold 5. Area 7 of the support between the cut 6 and the fold 5 is provided with an adhesive 8 such that the said area 7 adheres more strongly to the corresponding area of the other part of the support 4b than to the plastic film 2. This invention facilitates application of the dressing to skin.

7 Claims, 1 Drawing Sheet

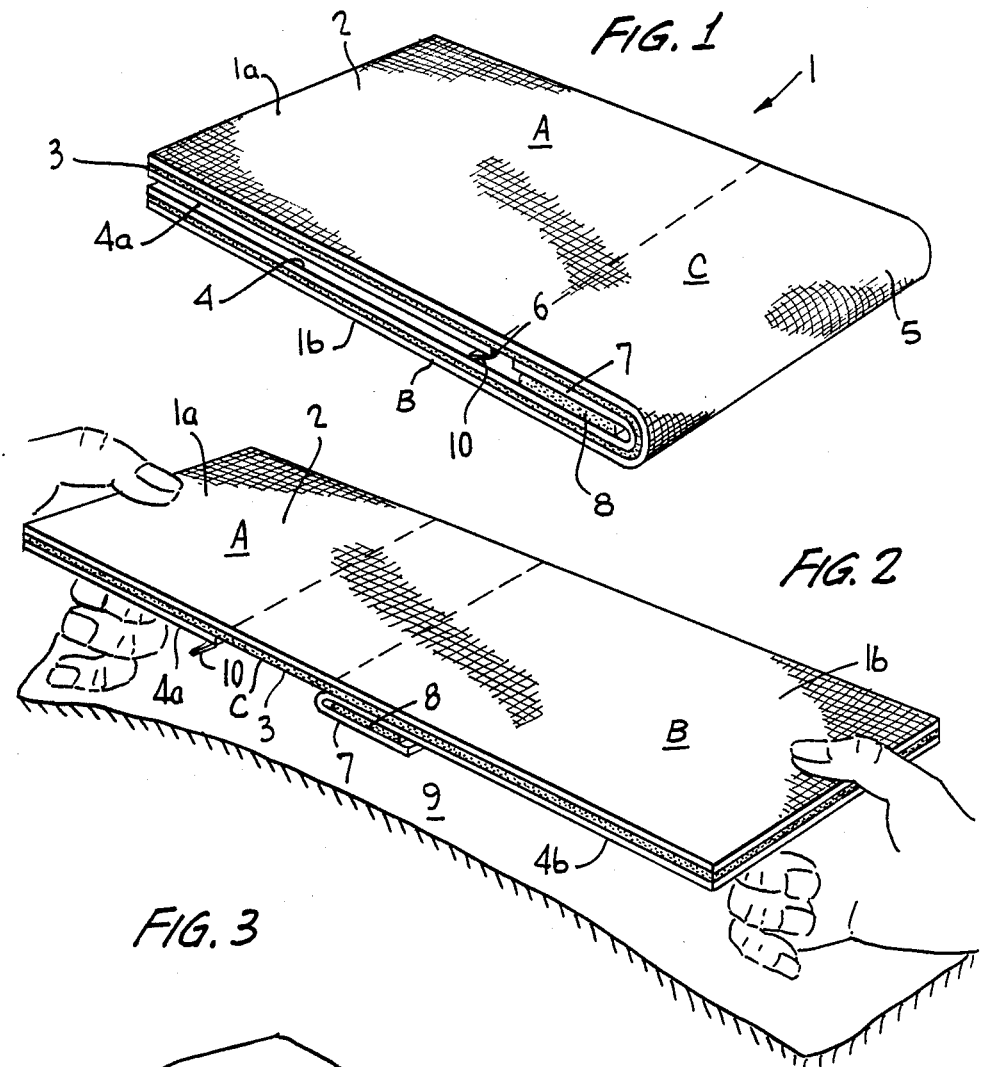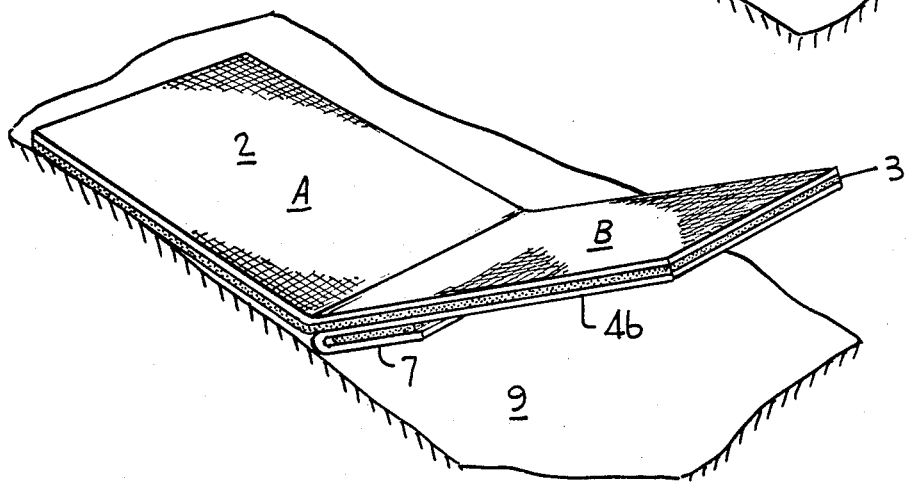

ADHESIVE DRESSING FOR EASY APPLICATION TO SKIN

FIELD OF THE INVENTION

The present invention relates to adhesive articles used to cover human and animal skin. The invention relates to an adhesive dressing which is easy to apply to skin because of a combination of special features. The dressing comprises a plastic film coated on one surface with a pressure-sensitive adhesive and a non-adhesive support protecting this adhesive before use.

BACKGROUND OF THE INVENTION

Adhesive articles and their use as dressings are well known and have been the subject of many patent applications. French Pat. Nos. 1025117, 1288390 and 2012584 describe adhesive dressings composed of a synthetic or natural plastic film, provided with a pressure-sensitive adhesive and a non-adhesive support, such as siliconized paper, protecting the adhesive. The plastic film is very thin (on the order of 20 microns) and flexible, and tends to adhere to itself and form folds when the support is pulled off before positioning on the skin. These folds make use of the dressing difficult or even impossible, since they prevent the dressing from assuming the contours of the skin, which is necessary for effective protection of the wound.

Several solutions have been proposed for avoiding this drawback. One such is described in European Patent Application No. 0051935. This solution consists in using a rigid support that does not adhere to the plastic film as strongly as the adhesive that keeps the film in place on the skin. This support is attached to the surface of the film that lacks adhesive. Thus when the support protecting the adhesive is pulled off before positioning of the dressing, the plastic film is held flat by the rigid support. The film is then applied to the skin and the rigid support can be removed since it adheres weakly to the plastic film. This device does, however, require the use of an additional support. This is true also of European Patent Application No. 0081890.

European Patent Application No. 0081889 describes another solution, in which both the protective support and the film of the adhesive dressing are scored on either side of a central zone. To apply the dressing, the central section of the protective support is removed, the dressing is affixed to the skin, and the outer sections of the support and film are then pulled away leaving the central zone stuck to the skin. This device is complex since matching incision lines must be made in the protective support and film. Besides, the outer sections of the plastic film are unused since they are removed with the rest of the support.

It is an object of the present invention to provide a simple and easily made dressing which enables the drawbacks described above to be avoided. The invention relates to a dressing which can be affixed by one person and which is economical, since it does not require removal of part of the plastic film.

GENERAL DESCRIPTION OF THE INVENTION

The dressing of the present invention is characterized in that:

1. It is folded back on itself on the side of the protective support along a transverse fold.
2. The protective support of one of the two parts is scored parallel to the fold.
3. The area of the support between the score line and the fold is provided with an adhesive such that the said area adheres more strongly to the corresponding area of the other part of the support than to the plastic film.

The dressing can be folded back on itself in two equal parts, but it may be preferable that one part slightly overlaps the other to facilitate grip.

The score line can be a line of weakness obtained by perforation or a preferred complete cut which allows separation without tearing.

The function of the area of the dressing that corresponds to the area of the support between the score line and the fold is, once it has been uncovered, to allow the dressing to be positioned. Hence the size of the said area of the support can be varied quite considerably according to the present invention. In general, the size of the said area will be relatively small in the case of small dressings and larger for large dressings.

The adhesive which binds the two areas of the support can be chosen without restriction from among double-sided adhesives, hot-melt adhesives or pressure-sensitive adhesives. Above all it is important that the bond between the two areas of the support is stronger than the bond between the support and the film. Those skilled in the art will easily be able to choose a suitable adhesive in light of these considerations. The choice may depend on the nature of the outer surface of the support. The support generally comprises a paper coated on its inside surface with silicone. Silicone is non-adhesive and so in this case it is possible to bind the two areas of the support with the same adhesive as that which covers the film, since the bond between the film and the siliconized paper will always be weaker than the paper-paper bond. However, preferred are hot-melt adhesives.

The dressing of the present invention can also include the addition of grip-tabs for easier unsticking of that part of the support constituted by one of the parts and the area between the score line and the fold, and of the complement of the other part of the support.

BRIEF DESCRIPTION OF THE DRAWINGS

The accompanying drawings illustrate, by way of example, a preferred embodiment of the dressing according to the present invention. In the drawings:

FIG. 1 shows a perspective view of an embodiment of a dressing according to the invention;

FIG. 2 shows a perspective view of the same dressing unfolded;

FIG. 3 shows a perspective view of the dressing partly affixed to the skin.

DESCRIPTION OF THE PREFERRED EMBODIMENT

As illustrated in FIG. 1, the embodiment of the dressing according to the invention is constituted by the rectangular dressing 1 which includes a plastic film 2 permeable to water vapor, such as a film of thermoplastic polyurethane or of polyamide, or of any other material with the same elastic properties. The said film is coated on one side with an adhesive 3 which is non-irritating to the skin, such as the polyacrylate adhesives described in U.S. Pat. No. 2,884,126, and which is itself covered with a non-stick protective support 4 constituted, for example, by siliconized paper.

Dressing 1 is folded back on itself on the side of the protective support 4 along a transverse fold 5, to give two equals parts 1a and 1b.

Part 4a of the protective support corresponds to part 1a of the dressing and is cut in a line 6 across its whole width, near to and parallel to the fold 5.

The protective support 4a includes area 7, which extends from the cut 6 to the fold 5 and which is stuck to the corresponding area 4b of the support 4 using a hot-melt adhesive 8 such that area 7 adheres more strongly to the corresponding area of the support 4b than to the plastic film 2. A tab 10 is stuck to the edge of the cut 6 in order to facilitate unsticking of the complementary part 4a of area 7.

As illustrated in FIGS. 2 and 3, parts 1a and 1b are unfolded when the dressing is positioned. Part 1a comprises the protective support 4b and area 7 which remains attached to the said support. As area 7 of the support remains attached to the corresponding part 4b of the support, part of the film is uncovered and this is applied to the skin and is held taut by pulling the ends of parts 1a and 1b. Support 4a is then removed by pulling the tab 10 and the whole of part 1a is applied to the skin. Support 4b and area 7 of support 4a are then removed and part 1b of the film is applied to the skin.

We claim:

1. An adhesive dressing rectangular or substantially rectangular in shape comprising in combination:

a thin, flexible plastic film having two major surfaces, a coating of an adhesive (3) on one of said surfaces, and a protective support positioned on said adhesive;

said dressing being folded onto itself along a transverse line to form two parts A and B, and whereby said plastic film forms the outermost surface of said combination of film, adhesive coating and protective support, and said protective support forms the innermost surface of said combination of film, adhesive coating, and protective support;

said protective support having a transverse rupture line spaced from said transverse fold line to form an area C between said transverse fold line and said rupture line;

a coating of adhesive (8) on the inner surface of said protective support at area C, said adhesive (8) being a stronger adhesive for said protective support than is said adhesive (3) for said protective support, whereby when said parts A and B are separated from each other by unfolding said dressing said protective support at area C adheres to said adhesive (8) to expose adhesive (3) at area C.

2. The adhesive dressing of claim 1 wherein said transverse rupture line is a complete cut which allows separation without tearing.

3. The adhesive dressing of claim 1 wherein said transverse rupture line is a perforated line.

4. The adhesive dressing of claim 2 wherein said parts A and B are of equal dimension.

5. The adhesive dressing of claim 2 wherein parts A and B are of unequal dimension, and one of said parts slightly overlaps the other of said parts.

6. The adhesive dressing of claim 1 wherein said protective support includes a tongue fixed to the edge of said rupture line so as to facilitate separation of said protective support from said adhesive coating (3).

7. The method of forming an adhesive dressing comprising the steps of:

(1) providing a thin, flexible plastic film having two major surfaces, a coating of adhesive (3) on one of said surfaces, and a protective support positioned on said adhesive;

(2) folding said adhesive dressing of (1) onto itself along a transverse line to form two parts A and B, and whereby said plastic film forms the outermost surface of said combination of film, adhesive coating and protective support, and said protective support forms the innermost surface of said combination of film, adhesive coating and protective support;

(3) providing a transverse rupture line on said protective support spaced from said transverse fold line to form an area C between said transverse fold line and said rupture line; and (4) providing a coating of adhesive (8) on the inner surface of said protective support at area C, said adhesive (8) being a stronger adhesive for said protective support than is adhesive (3) whereby when said supports A and B are separated from each other, said protective support at area C adheres to said adhesive (8) to expose said coating of adhesive (3) at area C.

* * * * *